US006767521B1

(12) United States Patent
Vogt et al.

(10) Patent No.: US 6,767,521 B1
(45) Date of Patent: Jul. 27, 2004

(54) SYSTEM FOR HANGING A DEHUMIDIFYING AND DEODORIZING POUCH

(75) Inventors: Fred K. Vogt, The Woodlands, TX (US); Surendra Kumar Mishra, The Woodlands, TX (US); David Prince Heaner, Martland, FL (US)

(73) Assignee: W.M. Barr & Company, Memphis, TN (US)

( * ) Notice: Subject to any disclaimer, the term of this patent is extended or adjusted under 35 U.S.C. 154(b) by 0 days.

(21) Appl. No.: 09/569,552

(22) Filed: May 12, 2000

Related U.S. Application Data

(63) Continuation-in-part of application No. 09/392,241, filed on Sep. 9, 1999, now abandoned.

(51) Int. Cl.[7] .............................. A61L 9/00; F26B 19/00; A24F 25/00; B65D 85/00; B65D 43/00

(52) U.S. Cl. ..................... 422/306; 422/305; 34/71; 34/80; 34/81; 34/82; 239/34; 239/37; 239/47; 239/51.5; 239/52; 239/57; 206/0.5; 229/125.01; 229/125.12; 96/4; 96/118; 96/147; 96/148; 96/222; 95/91

(58) Field of Search ..................... 422/1, 5, 28, 120, 422/305–306; 34/71, 80–82; 239/34, 37–41, 47–48, 51.3, 52–55, 57, 60; 206/0.5; 229/125.01, 125.12; 96/4, 118, 147–148, 222; 95/91

(56) References Cited

U.S. PATENT DOCUMENTS

| | | | |
|---|---|---|---|
| 3,722,182 A | 3/1973 | Gilbertson .................... 55/124 |
| 4,588,505 A | 5/1986 | Walley et al. ............ 210/502.1 |
| 4,840,773 A | 6/1989 | Wade .......................... 422/124 |
| 5,148,613 A | 9/1992 | Cullen ........................... 34/81 |
| 5,324,448 A | 6/1994 | Mayeaux ..................... 252/194 |
| 5,478,505 A | 12/1995 | McElfresh et al. ........... 261/30 |
| 5,657,866 A | 8/1997 | Kaneko et al. ............... 29/407 |
| 5,660,868 A | 8/1997 | Yeager ........................ 426/124 |
| 5,698,166 A | 12/1997 | Vick et al. ................... 422/124 |
| 5,907,908 A | 6/1999 | Cunanan et al. ............... 34/61 |

*Primary Examiner*—Robert J. Warden, Sr.
*Assistant Examiner*—Monzer R. Chorbaji
(74) *Attorney, Agent, or Firm*—Baker, Donelson, Bearman, Caldwell & Berkowitz

(57) ABSTRACT

A system for dehumidifying and deodorizing, the system comprising a hanging, dehumidifying and deodorizing pouch comprising a housing having a impermeable membrane and a semi-permeable securely attached to the impermeable membrane. The housing enclosing moisture-absorbent material and deodorizing material. The housing is enclosed within a jacket comprising a perforated contiguous wall; the wall defines an opening for receiving the housing. The jacket further comprises a closing member for closing the opening when the housing is within the jacket. The jacket can comprise a rigid, rectangular cage having a detachable lid. The semi-permeable membrane of the housing can comprise polyethylene or expanded polytetrafluoroethylene, individually or a combination thereof. The impermeable can comprise either polyethylene film or polypropylene film. The moisture-absorbent material can comprise a hygroscopic, deliquescent or a combination of a hygroscopic deliquescent and a gel forming polymer.

27 Claims, 4 Drawing Sheets

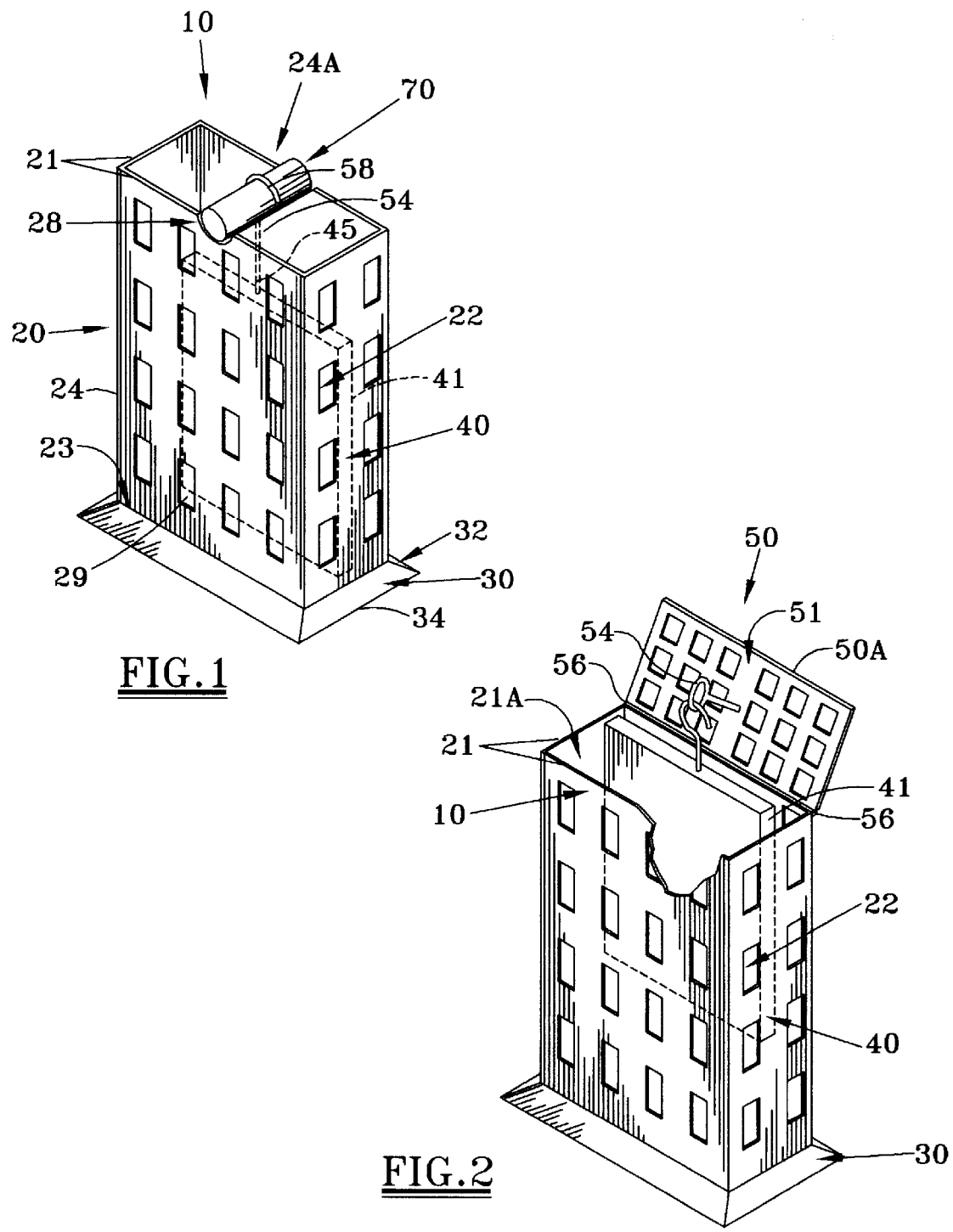

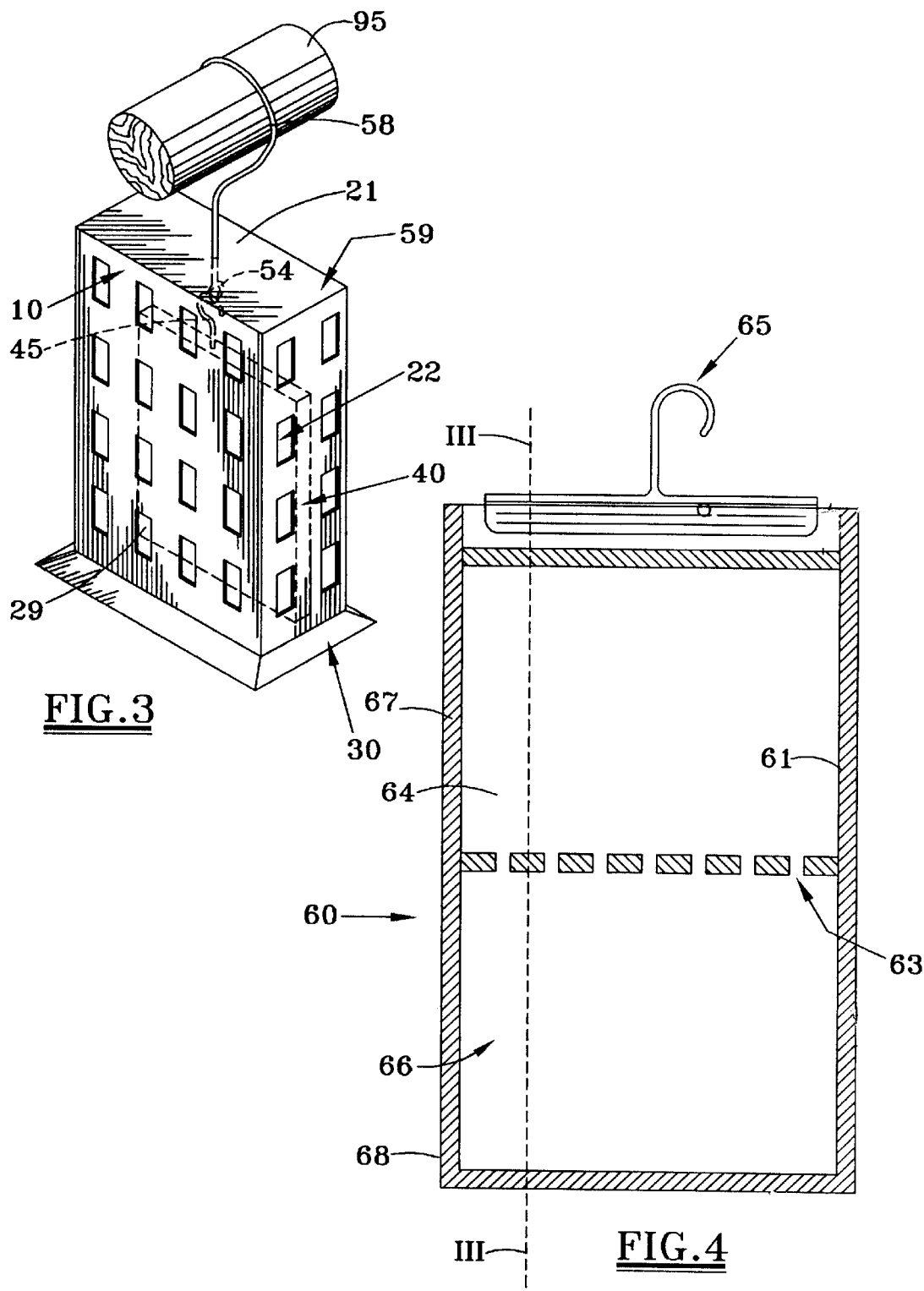

SYSTEM FOR HANGING A DEHUMIDIFYING AND DEODORIZING POUCH

CROSS-REFERENCE TO RELATED APPLICATIONS

This Application is a Contination in Part of U.S. patent application Ser. No. 09/392,241, and claims the benefit of priority to U.S. patent application Ser. No. 09/392,241, filed Sep. 9, 1999, for "Assembly for Dehumidifying and Deodorizing Automobiles, Boats and Other Motorized Vehicles."

FIELD OF THE INVENTION

The present invention relates to a system for dehumidifying and deodorizing. Particularly, a system that encloses and suspends a dehumidifying and deodorizing pouch within a jacket.

BACKGROUND OF THE INVENTION

Atmospheric water vapor in high humidity environments can be problematic to personal articles, clothing for example, and other items which are susceptible to corrosion, molding, mildewing, and other types of water related damage and deterioration. This typically occurs in situations where air conditioners are not run full time or cannot be run full time. Also, the interior of automobiles, boats and airplanes that are subjected to wet and humid weather conditions can develop odors as well as mildew and mold, and can rot from constant exposure to humid air. Older vehicles or housing with poor sealing, especially rainy climates are especially vulnerable to damage cause by humidity. Placement or positioning of the dehumidifying device can be a problem since the dehumidifying substances can cause damage or corrosion to the articles to be kept dry.

Commercially, atmospheric water vapor is problematic where there are hydrophilic materials present. Some of the problems high humidity can cause are caking of dried powder and granular substances, and water contamination pf organic liquids, like intermittently opened containers of organic liquids, especially internal combustion engine fuels, such as gasoline. A variety of partial solutions for the absorption of water, have evolved or have been developed in efforts to address these problems.

For example, Walley et al., U.S. Pat. No. 4,588,505, discloses a weighted, open mesh pouch containing a water absorbant placed at the bottom of, for example, a gasoline drum. This device absorbs water only from a liquid phase, but does not prevent the initial water contamination from forming. The pouch rests on the bottom of barrel.

Mayeaux, U.S. Pat. No. 5,324,448, suggests a packet which includes a composition that combines a desiccant and a vaporous corrosion inhibitor in situations where electronic components are subjected to atmospheric humidity.

A number of additives are known in the art for preventing such caking or clumping of powders and granules, such as salts, sugars, amino acids. For example, such as aluminum silicate can prevent the clumping of table salt. For this scenario, Kaneko et al., U.S. Pat. No. 5,657,866, provides a "double bag" packaging system which comprises inner water permeable and outer water impermeable liners and holds a desiccant between them.

Yeager, U.S. Pat. No. 5,660,868, teaches a dual compartment food storage bag with one compartment containing a soaker pad for absorbing liquids and the other compartment for containing food. While the overall bag is sealable, the two compartments communicate by means of perforations in a shared compartment wall between them. The storage bags are stacked when in use, see Yeager, col. 7, lines 25–30.

The above technologies have the limitation that the desiccants they use cannot be deliquescent. A deliquescent composition is one that melts away or dissolves gradually and becomes a liquid by attracting and absorbing moisture from the air. If a deliquescent composition were used in the above situations, the resultant liquid would itself be a contaminant. Further, because deliquescent derived liquids contain chemicals and have chemical properties different from pure water, in the case of contact with food, they could be toxic.

Cullen, U.S. Pat. No. 5,148,613 teaches a container having an upper portion and a lower portion divided by an elastic diaphragm having perforations and retaining deliquescent material. In Cullen, the liquid that is formed by the dissolving deliquescent material occupies the space that was previously occupied by the deliquescent material. The Cullen device rests on a surface.

Gilbertson, U.S. Pat. No. 3,722,182, discloses an air purifying and deodorizing device for automobiles. This device comprises a housing positioned on the rear window deck of the automobile and having air intake and air discharge openings. An electronic filtering device is mounted at the air intake opening for removing air-borne particles from the air taken into the device.

Furthermore, air freshening fragrance or scent dispensing devices are taught by McElfresh, et al., U.S. Pat. No. 5,478,505 ("'505"), Vick, et al. U.S. Pat. No. 5,698,166 ("'166"), and Wade, U.S. Pat. No. 4,840,773 ("'773"). McElfresh '505 discloses an air-treating device for dispensing a voltilizable material, such as air freshener fragrance, into the atmosphere of an enclosed area, such as an automobile interior. The device includes a housing and a reservoir of the volatiizable material therein, and a dual-configured, articulating attachment clip adapted for swingable motion for removable fastening of the device at a high air flow station such as a forced air vent grille on the interior of the vehicle. A device for scenting air in a forced air ventilation system is disclosed in Vick '166. An automobile deodorant dispenser revealed in Wade '773 comprises a liquid scent deodorant dispenser for utilization within a forced airstream.

The above technologies do not address or provide a solution to the problem of suspending dehumidifying or deodorizing pouches so the pouch does not spill and the contents of the pouch do not damage the surrounding clothing or other articles requiring protection from humidity. What is needed is a non-spillable, non-leaking hanging system housing an assembly for deodorizing and dehumidifying

SUMMARY OF THE INVENTION

The present invention provides a system for enclosing and suspending a dehumidifying and deodorizing pouch within a jacket. The system is used in close or closed environments, such as rooms, closets, storage containers, and motorized vehicles. The jacket protects the enclosed pouch hung within it from accidental jarring or bumping that could spill the contents of the pouch. Because the pouch is protected within the jacket, the system can be place on the floor or bottom of a container or hung in close proximity to items requiring the dehumidifying features of this invention. With a two-compartment pouch, such as the dehumidifying pouch disclosed in Cunanan et al., U.S. Pat. No. 5,907,908, incorporated herein in its entirety by reference, the jacket provides a means for suspending the pouch so that the dehumidfying material drips down to a collection compartment as it deliqueses. Preferably, the jacket has contiguous walls that are vented or perforated, a means for suspending the dehumidifying and deodorizing pouch, and a means for the jacket to attach to or rest on a surface. Further, the entire system, or merely the dehumidifying and deodorizing pouch can be disposable when the dehumidifying and deodorizing agents are spent.

BRIEF DESCRIPTION OF THE DRAWINGS

FIG. 1 is a perspective view of one embodiment of the invention depicting the housing suspended within the jacket.

FIG. 2 is a perspective view of one embodiment of the system of the present invention depicting the jacket with a hinged lid in an open position.

FIG. 3 is a perspective view of one embodiment of the system of the present invention depicting the jacket with a hinged lid in a closed position.

FIG. 4 is a cross-sectional view of one embodiment of the invention depicting the pouch.

DETAILED DESCRIPTION OF THE INVENTION

Figure 5:
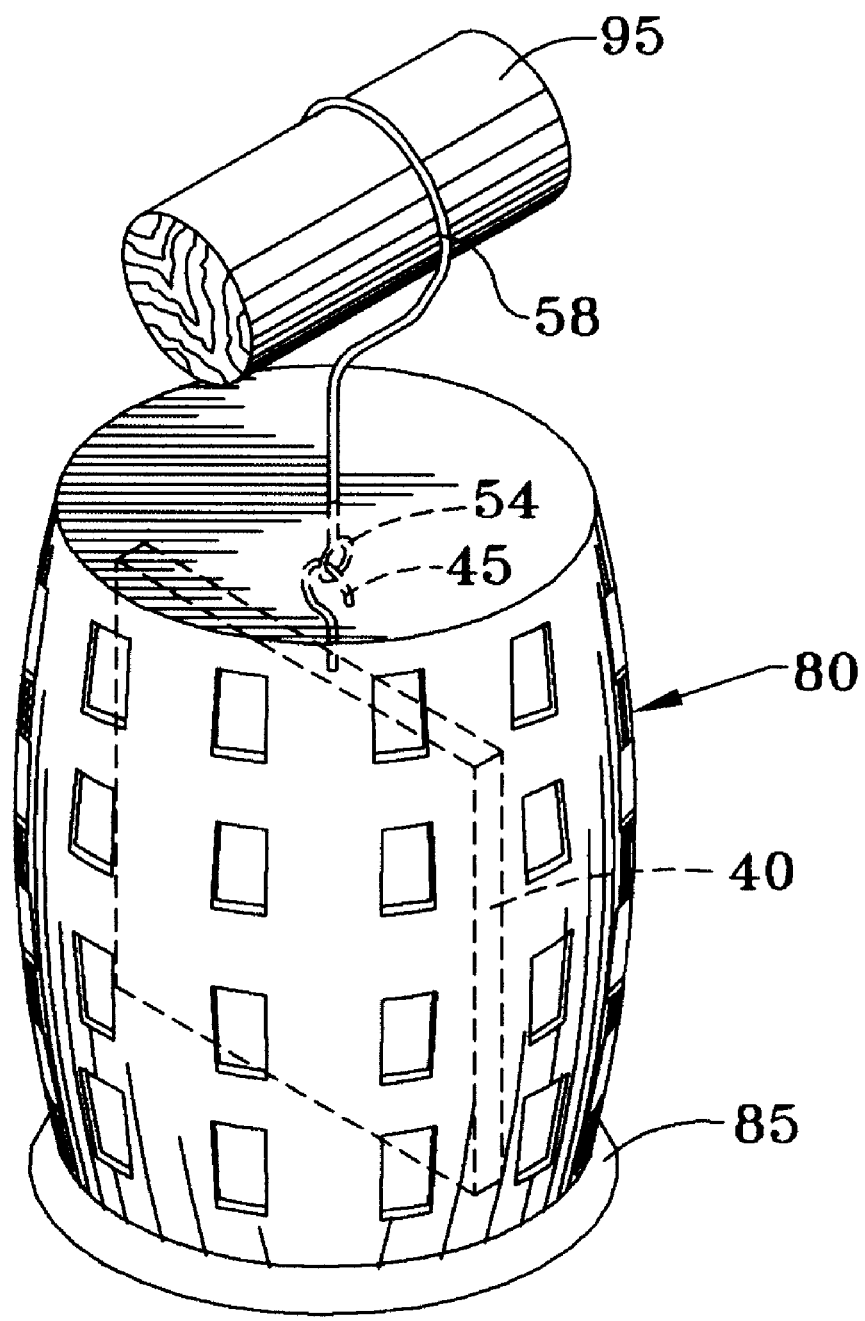
FIG. 5 is a perspective view of one embodiment of the system of the present invention depicting a rounded jacket
Figure 6:
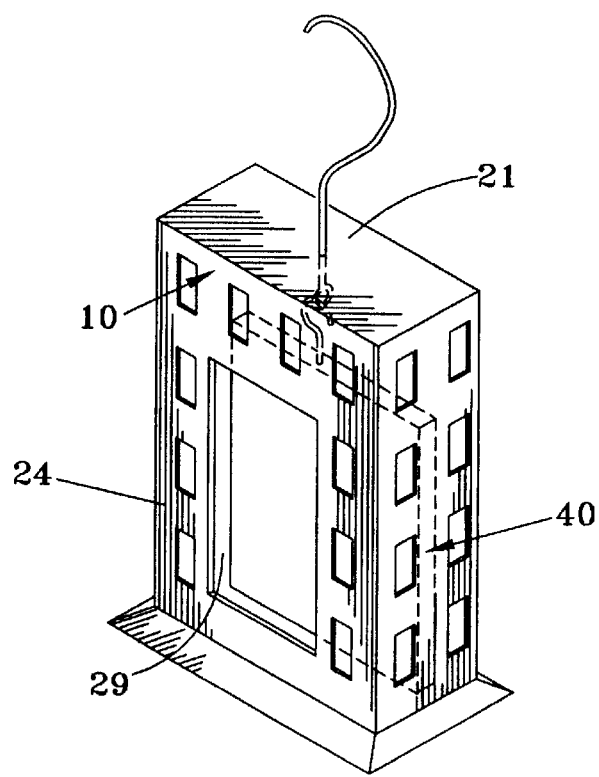
FIG. 6 is a perspective view of one embodiment of the present invention illustrating an opening in the front wall of the jacket.

The present invention relates to a system 10 for enclosing and suspending a dehumidifying and deodorizing pouch 40 within a jacket 20. The system 10 can be used in close or closed environments, such as rooms, closets, storage containers, and motorized vehicles. The jacket 20 protects the enclosed pouch 40 hung within it from accidental jarring or bumping that could pierce or puncture the pouch 40, causing spillage and/or leakage of the contents of the pouch 40. Advantageously, because the pouch 40 is protected within the jacket 20, the system 10 can be place on the floor or bottom of a container or hung in close proximity to items requiring the dehumidifying features of this invention, such as clothing. A pouch hanger 45 can be attached to the pouch 40 so that the pouch 40 can be hung.

With a two-compartment pouch 60 as illustrated in FIG. 4, and disclosed in Cunanan et al., U.S. Pat. No. 5,907,908, incorporated herein in its entirety by reference, the jacket 20 provides a means for suspending a two compartment pouch 60 within a protective enclosure so that the dehumidfying material in a first compartment 64 drips down to a collection compartment 66 as it deliqueses.

Preferably, the jacket 20 has contiguous walls 24 that are vented or perforated. The walls define an interior compartment 29 for receiving the hanging pouch 40. The jacket 20 further comprises a means for suspending 54, 70 the dehumidifying and deodorizing pouch 40, 60, a hook or eyelet, for example, as shown in FIGS. 1 and 2. The means for suspending 54, 70 engages with the pouch hanger 45 attached to the pouch 40. The jacket 20 further comprises a means 30 for the jacket 20 to attach to or rest on a surface. Alternatively, referring to FIG. 3, the jacket 20 can also comprise a means for hanging 58 the jacket so that the system 10 can be hung within a closed environment, a clothing rod within a closet for example. Further, the entire system 10, or merely the dehumidifying and deodorizing pouch 40, 60 can be disposable when the dehumidifying and deodorizing agents are spent. A preferred pouch 40, is disposable and comprises a non-spillable housing 41, preferably manufactured from inexpensive materials. The pouch 40 is enclosed within the porous jacket 20.

In one preferred embodiment of the invention as referenced in FIG. 1 and FIG. 4, a system for dehumidifying and deodorizing 10 comprises a hanging pouch 40, 60. The hanging pouch 40, 60 can comprise one compartment or preferably, two compartments 64, 66. The pouch 40, 60 comprises a housing 41, 61 that is formed from an impermeable membrane 68 and a semi-permeable membrane 67 securely attached to the impermeable membrane 68 as shown in FIG. 4. Preferably, the housing 41, 61 encloses moisture absorbent material and a deodorizing material. The jacket 20 for enclosing the housing 41, 60 comprises contiguous side walls 24 and a bottom wall 23, the walls 23, 24 defining an interior compartment 29 for receiving the hanging pouch 40. The side walls further define perforations 22 to allow fluid communication between the pouch 40 and the atmosphere when the hanging pouch 40 is within the interior compartment 29. The perforations 22 enable moisture from the surrounding atmosphere to be drawn into the jacket 20 and absorbed by the moisture-absorbent material within the housing 41, 61. At the same time, deodorant within the housing 41, 61 can be emitted from the housing 41, 61 through the perforations 22 to the surrounding environment. The bottom wall 23 can form a base 30 for the system 10.

Referring to FIGS. 1, 2 and 3, the top 21 of the jacket 20 can define an opening 21A that is sized to allow insertion of the pouch 40 into the interior compartment 29. Preferably, the jacket 20 comprises a closing member 50 adapted to close the opening 21A after insertion of the housing 41 into the jacket. Other embodiments of this invention (not shown) can have the opening positioned in different walls of the jacket 20, the side walls 24 or the bottom 23, for example. In one aspect, the top 21 of the jacket 20 can define an opening 21A as shown in FIG. 1. A closing member 50 can comprise a lid 50A that can be fixedly attached to the top 21 of the jacket 20. In an alternative embodiment, not shown, the top closing member is integral with the side walls 24 and the opening for insertion of the pouch is in a side wall 24. In another embodiment as illustrated in FIG. 2, the top 21 can be a lid 50A that is hingedly attached so that the lid 50A opens to allow insertion of the pouch 40. Perforations 22 in the jacket 20 and lid 50A permit the exchange between the atmosphere and the housing so that moisture can be absorbed and deodorant released. When the moisture-absorbent is consumed, the lid 50A can be opened and the housing 41 replaced.

In another aspect of this invention, the top 21 can comprise a first means 70, 54 for engaging the pouch 40, 60 with the top 21. The pouch 40, 60 comprises a second means 45, 65, a pouch hanger 45 for example, for engaging the pouch 40, 60 with the top 21 so that when the first means 70, 54 is engaged with the second means 45, 65, the pouch 40, 60 depends from the top 21. Referring to FIG. 1, one preferred embodiment comprises contiguous walls having a top ends 24A and bottom ends, the top ends 24A of two opposing contiguous walls 24 define one or more grooves 28. Preferably, a spindle 70 is adapted to fit within two opposing grooves 28. The second means 45, 65 for engaging the pouch to the top 21 can comprise a pouch hanger 45. When the pouch hanger 45 engages the spindle 70, the pouch depends from the spindle 70 towards the bottom 23.

In an alternative first means 54 for engaging the pouch to the top 21 as depicted in FIG. 2, the jacket comprising contiguous side walls 24, a top wall 50 or lid 50A hingedly connected to one of the side walls 24, and a bottom wall 23. The jacket 20 defines an opening 21A sized to allow insertion of the hanging pouch 40 into the interior compartment 29 when the top wall 50 is in an open position. Preferably, the top wall 50 or lid 50A has an interior surface 51 adjacent the opening 21A defined by the jacket 20 and an exterior surface 59. Hinges 56 allow the lid 50A to open and close. The interior surface 51 of the lid 50A comprises the first means 54 for engaging the pouch. In one embodiment the first means 54 is a hook 54. Alternatively, the first means can be a circular hanger, an eyelet for example. In this embodiment, the housing further comprises a pouch hanger 45 for engaging the hook 54 so that the pouch 40 depends from the hook 54.

The jacket 20 further comprises a bottom wall 23. In one embodiment, FIG. 1, wherein the system can be placed on a surface such as the floor of a closet or ledge of an automobile, the bottom wall 23 can comprise a base 30 for the system. In this embodiment, the base comprises a top base 32 and a bottom base 34. Preferably, base 30 widens from the top base 32 to the bottom base 34 so that the system 10 is stablized when free standing. Alternatively, the jacket 20 can be configured to hang from a rod such as a clothing rod 95 or other device. As illustrated in FIG. 3, the jacket can comprise a jacket hanger 58 attached to the exterior surface 59 of the lid 50A.

FIGS. 1, 2 and 3 illustrate a jacket 20 that is a rigid, rectangular box. Alternatively, the jacket 80 can be rounded as illustrated in FIG. 5. The shape and rigidity of the jacket 20 can vary and are not limited to the shapes illustrated in the drawings. Various shapes and rigidity are within the scope of this invention, a pyramid, character design or oval, for example, as long as the resulting shape of the jacket is stable if resting on a flat surface of depending from a clothing rod 95 which engages with the jacket hanger 58 of FIG. 3. FIG. 2 depicts the embodiment of the jacket 20 having a lid 50A that is attached to a contiguous wall 24 by hinges 56. The lid 50A is in open position for inserting or removing the pouch 40. FIG. 3 depicts the hinged lid 50A in a closed position with the pouch 40 inside the jacket 30. Alternatively, the jacket 20 can comprise a casing or plastic envelop for containing the housing 51 (not shown). In this embodiment, the casing comprises a contiguous wall that defines a closable opening (not shown). A zipper can be used to open and close the opening so that housing can be inserted. The casing or plastic envelope can preferably be manufactured from, but not limited to, polyethylene, polytetrafluroethylene, polypropylene and the like.

In one embodiment as described above, the jacket bottom 23 is widened to form a stabilizing base 30 that is adapted to resting upon a surface. In an alternative embodiment, the top 21 or side of the jacket 20 attaches to a surface so that the entire system is suspended from a ceiling or wall. Velco® type adhesive is one means of adhering the jacket 20 to a ceiling or wall. Other means and adhesives are know in the art.

In another preferred embodiment, the pouch 60, as illustrated in FIG. 4, comprises two housings 61, 68 defining two compartments 64, 66. One compartment 64 absorbs moisture vapors from the surrounding atmosphere, the other compartment 66 receives liquid moisture from the moisture-absorption compartment 64. The moisture-absorption compartment 64 can contain a deliquescent desiccant and can also optionally include a deodorant and/or air freshener. In this preferred embodiment, a hanger 65 is used so that the pouch 40 can be hung within the jacket 20.

In one preferred embodiment, the jacket 20 further comprises a jacket hanger 58 so that the system 10 can be hung above the ground or floor. Preferably the jacket hanger 58 is comprised of a polymer having enough strength to bear the weight of the system 10 when it is at its fullest with desiccant and liquid.

In another aspect of this invention shown in FIG. 4, the moisture-absorption compartment 64 comprises semi-permeable material, preferably a membrane, that allows diffusion of moisture vapors into the moisture-absorption compartment 64. The diffusion is not reversible under normal use conditions. Preferably, the semi-permeable membrane is a polymer material. More preferably, the semi-permeable membrane comprises polyethylene, commonly. sold under the tradename, TYVEK®, or, expanded polytetrafluoroethylene, available under the mark, GOR-TEX®. In one embodiment, the entire moisture-absorption compartment 64 is comprised of semi-permeable material. Alternatively, the moisture-absorption Pouch 60 is comprised in part of semi-permeable material and in part moisture-impervious material. The rate of moisture uptake by the moisture-absorption compartment 64 is controlled by the amount of semi-permeable material used to make the compartment 64. Moisture uptake can be reduced by reducing the amount of semi-permeable material used to form the moisture-absorption compartment 60.

Figure 7:
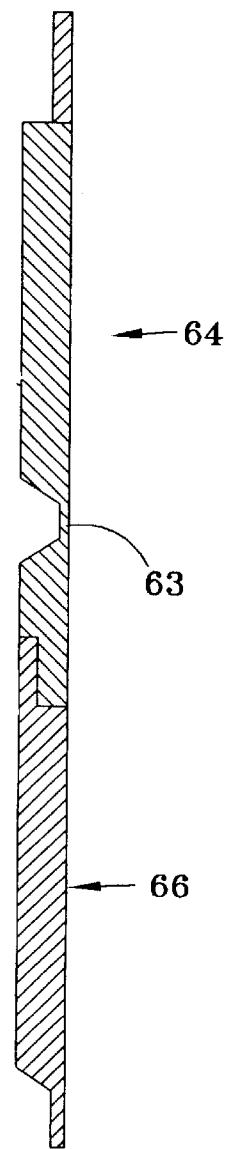
FIG. 7 is a side view of the front panel of the pouch 60.

FIG. 4 illustrates a two-compartment pouch 60 that absorbs the moisture in the upper compartment 64 containing deliquescent material and collects the moisture in the lower compartment 66. The two-compartment pouch is comprised in part of semi-permeable material and comprised in part by moisture-impervious material. In this preferred embodiment of the two-compartment pouch 60, the pouch 60 has a front side and a back side. FIG. 4 and FIG. 7 show the front side that is comprised of an upper panel 67 and a lower panel 68. Semi-permeable material or membrane 67 is used as the front upper panel 67 of the moisture-absorption compartment 64 to allow moisture to seep in from the surrounding environs. The bottom of the front panel is comprised of moisture impervious material (an impermeable membrane) 68 to retain the collected moisture in the bottom of the pouch 60. Preferably, the back side of the pouch is comprised of impermeable material.

In one preferred embodiment, the housing 61 of the pouch 60 comprises a back side and a front side: the front comprising a two panels 67, 68 (a semi-permeable upper panel 67 and an impermeable bottom panel 68) and a single back panel (not shown) that is sealed to the front panel along their edges with a secure, solid seal and across the middle by a broken seal 63. Sealing across the middle allows the housing 61 to define two compartments, an upper compartment containing deliquescent material for moisture absorption and a lower compartment for moisture collection. In this way, liquids from the moisture-absorption compartment 64 can flow down by gravity through the broken seal and into the collection compartment 66. The front panel 67 is formed from two different materials, semi-permeable material in the area of the moisture-absorption compartment 64 and moisture-impervious material in the area of the collection compartment 66. Because water vapor pressure is greater in the surrounding atmosphere, moisture vapors enter the pouch 60 by passing through the semi-permeable membrane 67 in the area of the moisture-absorption compartment 64. The vapors are absorbed by the desiccant until it deliquesces, and the deliquescent then flows down into the collection compartment 66.

One embodiment of the hanging pouch 40 of this invention comprises semi-permeable membrane on one side of the moisture-absorption compartment 64 in a two-compartment pouch 60. Preferably, the opposite side of the moisture-absorption compartment 64 and the collection compartment 66 are comprised of moisture-impervious or impermeable material. The pouch 40 can comprise two panels: a two-part front panel and a single back panel. The panels, are sealed along their top edges and side edges and sealed with a broken seal in the area that separates the moisture absorption compartment 64 from collection compartment 66 so that liquids from the moisture-absorption compartment 64 can flow down by gravity into the collection compartment 66. Because water vapor pressure is greater in the surrounding atmosphere, moisture vapors enter the pouch 60 by passing through the semi-permeable membrane in the area of the moisture-absorption compartment 64, the vapors are absorbed by the desiccant until it deliquesces, and the deliquescent then flows down into the collection compartment 66.

In an alternate embodiment (not shown), a moisture-impervious cover material can be removably attached to the semi-permeable material so that the user can vary the rate of moisture uptake by removing the cover material either in its entirety or in part, depending how fast the user desires the moisture uptake to be. The more cover that is removed, the more moisture is absorbed through the semi-permeable material. In another aspect of the invention, all seals on the pouch 40, 60 should be tight enough to prevent leakage if dropped from a height of 10 feet when the moisture-absorption compartment 64 is filled with 16 ounces of desiccant and the collection compartment 66 is 75% full of liquid.

The desiccant contained within the hanging pouch 40, 60 absorbs moisture vapors and the desiccant becomes saturated with moisture vapors and deliquesces. Because the materials comprising the pouch 40, 60 are inexpensive, the system 10 may be disposed when the pouch 40, 60 is full even though the deliquescent desiccant could otherwise continue to absorb moisture vapors. Preferably, the desiccant material used for moisture absorption is preferably comprised of a salt selected from the group consisting of alkali metal halides, alkaline earth metal halides, iron halides and aluminum halides, individually or combinations thereof. Preferably, the desiccant material is comprised of calcium chloride. The deodorizing material can be activated carbon, zeolite or molecular sieves, individually or in combinations thereof. In an alternative embodiment, the desiccant material can further comprise a fragrance.

In still another aspect, the hygroscopic, deliquescent material used for moisture absorption is preferably comprised of a salt selected from the group consisting of alkali metal halides, alkaline earth metal halides, iron halides and aluminum halides, individually or combinations thereof. Preferably, the hygroscopic, deliquescent material comprises calcium chloride. Alternatively, the hygroscopic deliquescent is a gel. In still another alternative embodiment, the hygroscopic, deliquescent comprises magnesium chloride. The moisture-absorbent material can also comprise a combination of a hygroscopic deliquescent and a gel forming polymer. The gel forming polymer can be selected from but is not limited to, polyacrylates, polyacrylimide-polyacrylate co-polymers and polyacrylate-polyalcohol co-polymers. The deodorizing material can be activated carbon, zeolite or molecular sieves, individually or in combinations thereof. In an alternative embodiment, the system 10 can further comprise a fragrance.

For shipping and storage of any of the above-described embodiments of the system 10, the semi-permeable membrane portion of the housing 41, 61 is covered with a removable seal (not shown) to prevent moisture and/or odors from entering the system 10 and deodorant or fragrance from leaving the system 10. To activate the system 10, the removable seal is removed from the hanging pouch 40, 60, the pouch 40, 60 is placed within the jacket 20, and the jacket 20 is closed. The system 10 can be place in a container, room or closet requiring dehumidifying or in an inconspicuous place within an automobile, boat, airplane or other motorized vehicle. Under a seat or within an open compartment is preferred.

The foregoing description is illustrative and explanatory of preferred embodiments of the invention, and variations in the size, shape, materials and other details will become apparent to those skilled in the art. It is intended that all such variations and modifications which fall within the scope or spirit of the appended claims be embraced thereby.

What is claimed is:

1. A system for dehumidifying and deodorizing, the system comprising:
   a hanging, dehumidifying and deodorizing pouch, the hanging pouch comprising a housing, the housing comprising an impermeable membrane and a semi-permeable membrane securely attached to the impermeable membrane, the housing enclosing moisture absorbent material and a deodorizing material;
   a jacket for enclosing the hanging pouch, the jacket comprising contiguous side walls and a bottom wall, the walls defining an interior compartment for receiving the hanging pouch, the walls further defining perforations to allow communication between the hanging pouch and the atmosphere when the hanging pouch is within the interior compartment, the bottom wall forming a base for the system;
   the jacket defining an opening that is sized to allow insertion of the hanging pouch into the interior compartment;
   the contiguous walls having top ends and bottom ends, the top ends of the contiguous walls defining a groove;
   a spindle adapted to fit within two opposing grooves; and
   the hanging pouch further comprising a means for engaging the spindle so that the hanging pouch depends from the spindle.

2. The system of claim 1 wherein the hanging pouch further comprises a moisture-absorption compartment and a collection compartment;
   the moisture-absorption compartment comprising semi-permeable material enclosing deliquescent desiccant material and an optional deodorizing material;
   the moisture-absorption compartment connected to the collection compartment so that liquid moisture from the moisture-absorption compartment is transferred to the collection compartment, the collection compartment comprising impermeable membrane material.

3. The system of claim 1 wherein the housing is comprised of transparent material.

4. The system of claim 1 wherein the semi-permeable material comprises a polymer.

5. The system of claim 4 wherein the polymer comprises polyethylene or expanded polytetrafluoroethylene, individually or a combination thereof.

6. The system of claim 1 wherein the impermeable membrane material comprises a polymer.

7. The system of claim 1 wherein the impermeable membrane comprises polyethylene film.

8. The system of claim 1 wherein the impermeable membrane material comprises polypropylene film.

9. The system of claim 1 wherein the moisture absorbent material comprises hygroscopic, deliquescent material.

10. The system of claim 9 wherein the hygroscopic, deliquescent material comprises a salt selected from the group consisting of alkali metal halides, alkaline earth metal halides, iron halides and aluminum halides, individually or a combination thereof.

11. The system of claim 1 wherein the moisture absorbent material comprises a gel-forming polymer.

12. The system of claim 1 wherein the moisture absorbent material further comprises a fragrance.

13. The system of claim 1 wherein the deodorizing material comprises activated carbon, zeolite or molecular sieves, individually or in a combination thereof.

14. The system of claim 1 wherein the jacket is comprised of a rigid material.

15. The system of claim 1 wherein the jacket is box-shaped.

16. The system of claim 1 wherein the jacket is rounded.

17. The system of claim 1 wherein the jacket bottom is widened to form a stabilizing base and is adapted to resting upon a surface.

18. The system of claim 1 wherein one surface of the jacket comprises an attachable member so that the system is adapted to suspend from a ceiling or a wall.

19. The system of claim 1 wherein the jacket comprises a closing member adapted to close the opening sized to allow insertion of the hanging pouch into the jacket.

20. The system of claim 19 wherein the closing member is a lid.

21. The system of claim 1 wherein the housing is connected to a second housing, the second housing comprising a second semi-permeable membrane and a second impermeable membrane, the first housing enclosing moisture absorbent material and the second housing enclosing a deodorant.

22. A system for dehumidifying and deodorizing comprising:
   a hanging, dehumidifying and deodorizing pouch, the hanging pouch comprising a housing, the housing comprising an impermeable membrane and a semi-permeable membrane securely attached to the impermeable membrane, the hanging pouch enclosing moisture absorbent material and a deodorizing material;
   a jacket for enclosing the hanging pouch, the jacket comprising contiguous side walls, a top wall hingedly connected to one of the side walls, and a bottom wall, the walls defining an interior compartment for receiving the hanging pouch, the walls further defining perforations to allow communication between the hanging pouch and the atmosphere when the hanging pouch is within the interior compartment, the bottom wall comprising a base for the system;
   the jacket defining an opening sized to allow insertion of the hanging pouch into the interior compartment when the top wall is in an open position;
   the top wall having an interior surface adjacent to the opening defined by the jacket and an exterior surface, the interior surface comprising a means for suspending the hanging pouch; and
   the hanging pouch further comprising a means for engaging the means for suspending so that the hanging pouch depends from the means for suspending.

23. The system of claim 22 wherein the hanging pouch comprises a moisture-absorption compartment and a collection compartment;
   the moisture-absorption compartment comprising semi-permeable material enclosing deliquescent desiccant material and an optional deodorizing material;
   the moisture-absorption compartment connected to the collection compartment so that liquid moisture from the moisture-absorption compartment is transferred to the collection compartment, the collection compartment comprising impermeable membrane material.

24. A system for dehumidifying and deodorizing, the system comprising:
   a hanging, dehumidifying and deodorizing pouch, the hanging pouch comprising a first compartment comprising semi-permeable membrane, wherein the first semi-permeable membrane comprises a polymer and the first impermeable membrane comprises a polymer;
   the first compartment enclosing moisture absorbent material wherein the moisture absorbent material comprises a salt selected from the group consisting of alkali metal halides, alkaline earth metal halides, iron halides and aluminum halides, individually or a combination thereof; and
   a second compartment attached to the first compartment so that liquid from the first compartment is transferred to the second compartment, the second compartment comprising a impermeable membrane, wherein the impermeable membrane comprises a polymer;
   the first compartment enclosing a deodorant comprising activated carbon, zeolite or molecular sieves, individually or in a combination thereof;
   a jacket for enclosing the hanging pouch, the jacket comprising contiguous walls and a bottom wall, the walls defining an interior compartment for receiving the hanging pouches, the walls further defining perforations to allow communication between the hanging pouch and the atmosphere when the hanging pouch is within the interior compartment, the bottom wall forming a stabilizing base for the system;
   the jacket defining an opening sized to allow insertion of the hanging pouchs into the interior compartment;
   the jacket comprises a top and a bottom, the top comprising first means for engaging the first compartment with the top;
   the first compartment further comprising a second means for engaging the first compartment with the top so that the hanging pouch depends from the top end.

25. The system of claim 24 wherein the first and second compartments further comprise a removable protective cover over the semi permeable membranes to prevent exposure of the dehumidifier or deodorizer until ready for use.

26. The system of claim 24 wherein the jacket is a cage.

27. The system of claim 24 wherein the contiguous walls have top ends and bottom ends, the top ends of the contiguous walls defining a groove; the first means for engaging the first compartment comprising a spindle adapted to fit within two opposing grooves so that the first means engages with the second means and the first compartment depends from the spindle.

* * * * *